(12) United States Patent
Cowe et al.

(10) Patent No.: US 9,858,887 B2
(45) Date of Patent: Jan. 2, 2018

(54) PEN-TYPE DRUG INJECTOR WITH DOSE ENCODER HAVING PIEZOELECTRIC TRANSDUCERS AND ALPHANUMERIC SEGMENTED ELECTRONIC DISPLAY THEREFOR

(71) Applicant: OWEN MUMFORD LIMITED, Oxford (GB)

(72) Inventors: Toby Cowe, Oxford (GB); Cosimo Santella, Oxford (GB)

(73) Assignee: OWEN MUMFORD LIMITED, Oxford (GB)

( * ) Notice: Subject to any disclaimer, the term of this patent is extended or adjusted under 35 U.S.C. 154(b) by 0 days.

(21) Appl. No.: 14/648,569

(22) PCT Filed: Nov. 28, 2013

(86) PCT No.: PCT/GB2013/053148
§ 371 (c)(1),
(2) Date: May 29, 2015

(87) PCT Pub. No.: WO2014/083343
PCT Pub. Date: Jun. 5, 2014

(65) Prior Publication Data
US 2015/0302818 A1 Oct. 22, 2015

Related U.S. Application Data

(60) Provisional application No. 61/731,587, filed on Nov. 30, 2012.

(30) Foreign Application Priority Data

Nov. 30, 2012 (GB) .................................. 1221577.8

(51) Int. Cl.
*A61M 5/315* (2006.01)
*G09G 5/00* (2006.01)
(Continued)

(52) U.S. Cl.
CPC .................. *G09G 5/00* (2013.01); *A61M 5/24* (2013.01); *A61M 5/31525* (2013.01);
(Continued)

(58) Field of Classification Search
CPC .......... A61M 5/31551; A61M 5/31525; A61M 5/24; A61M 5/31553; A61M 5/31546;
(Continued)

(56) References Cited

U.S. PATENT DOCUMENTS 5,728,074 A * 3/1998 Castellano .......... G06F 19/3468
600/309
5,731,707 A * 3/1998 Andermo ............. G01D 5/2415
324/660
(Continued)

FOREIGN PATENT DOCUMENTS

CN        1705498 A    12/2005
CN     102202711 A     9/2011
(Continued)

OTHER PUBLICATIONS

International Search Report, dated Aug. 21, 2014, from corresponding PCT application.
(Continued)

*Primary Examiner* — Dismery Mercedes
(74) *Attorney, Agent, or Firm* — Young & Thompson

(57) ABSTRACT

A display arrangement for e.g. a medical substance delivery device includes a movable control member, at least one transducer responsive to movement of the control member to convert mechanical energy into electrical energy to output an electrical signal, a drive circuit for receiving the electrical signal and for outputting an output drive signal, and a display device for receiving the output drive signal and displaying a variable image that varies consequent on the relative movement. The display may be a bistable display, so
(Continued)

that the display function is self-powered without a requirement for a battery or the like. The parameter displayed for a medical substance delivery device may be a dose volume, a count of doses delivered, progress and/or completion of a dose. The drive circuit is an absolute position encoder and detects the actual position of the control member and does not deduce the position by counting pulses.

22 Claims, 14 Drawing Sheets

(51) Int. Cl.
| | | |
|---|---|---|
| *A61M 5/24* | (2006.01) | |
| *B41J 3/407* | (2006.01) | |
| *G09F 9/302* | (2006.01) | |
| *G06T 11/20* | (2006.01) | |
| G06F 19/00 | (2011.01) | |
| A61M 5/31 | (2006.01) | |
| G01D 5/249 | (2006.01) | |
| G09G 3/04 | (2006.01) | |
| G02F 1/1343 | (2006.01) | |

(52) U.S. Cl.
CPC ........ *A61M 5/31551* (2013.01); *B41J 3/4076* (2013.01); *G06T 11/206* (2013.01); *G09F 9/302* (2013.01); A61M 2005/3126 (2013.01); A61M 2205/0294 (2013.01); A61M 2205/3317 (2013.01); G01D 5/2497 (2013.01); G02F 1/134327 (2013.01); G06F 19/3468 (2013.01); G09G 3/04 (2013.01); G09G 2300/0473 (2013.01); G09G 2330/00 (2013.01)

(58) Field of Classification Search
CPC ............ A61M 5/31545; A61M 5/3158; A61M 5/31581; A61M 5/3159; A61M 5/31591; A61M 2205/3317; A61M 2205/8212; A61M 2205/52; G06F 19/3468; G09G 3/00

See application file for complete search history.

(56) References Cited

U.S. PATENT DOCUMENTS

| | | | | |
|---|---|---|---|---|
| 6,585,698 B1* | 7/2003 | Packman | ................. | A61M 5/24 604/207 |
| 6,942,646 B2* | 9/2005 | Langley | ............ | A61M 5/14244 604/207 |
| 8,257,318 B2* | 9/2012 | Thogersen | ........ | A61M 5/31585 604/110 |
| 8,556,866 B2* | 10/2013 | Krulevitch | .............. | A61M 5/24 604/186 |
| 9,186,465 B2* | 11/2015 | Jorgensen | ......... | A61M 5/31551 |
| 9,192,728 B2* | 11/2015 | Gilmore | ............ | A61M 5/31551 |
| 2005/0284471 A1* | 12/2005 | Bruna | ................. | A61M 15/009 128/200.23 |
| 2006/0011651 A1 | 1/2006 | Bruna | | |
| 2007/0135756 A1* | 6/2007 | Kohlbrenner | ......... | A61M 5/178 604/21 |
| 2009/0076460 A1* | 3/2009 | Nielsen | ................... | G01D 5/204 604/207 |
| 2009/0299279 A1 | 12/2009 | Rochter | | |
| 2009/0318865 A1* | 12/2009 | Moller | .............. | A61M 5/31553 604/135 |
| 2010/0286665 A1* | 11/2010 | Manna | .......... | A61B 17/320068 604/542 |
| 2010/0323431 A1* | 12/2010 | Rutkowski | ............. | G09G 3/006 435/286.1 |
| 2011/0270214 A1* | 11/2011 | Jorgensen | ......... | A61M 5/31551 604/500 |
| 2012/0101445 A1* | 4/2012 | Jansen | .................... | A61M 5/24 604/189 |
| 2014/0074041 A1* | 3/2014 | Pedersen | ................. | A61M 5/20 604/211 |
| 2014/0131388 A1* | 5/2014 | Heisel | ................. | A61M 15/009 222/36 |
| 2014/0144946 A1 | 5/2014 | Kohnle et al. | | |
| 2014/0163474 A1* | 6/2014 | Draper | ......... | A61M 5/31551 604/189 |

FOREIGN PATENT DOCUMENTS

| | | |
|---|---|---|
| DE | 10 2006 04753 A1 | 4/2008 |
| EP | 1 074 273 A1 | 2/2001 |
| EP | 2 182 456 A1 | 5/2010 |
| EP | 2 455 120 A1 | 5/2012 |
| WO | 98/19208 A2 | 5/1998 |
| WO | 99/10769 A1 | 3/1999 |
| WO | 2006/120182 A1 | 11/2006 |
| WO | 2007/099093 A1 | 9/2007 |
| WO | 2007/122253 A1 | 11/2007 |
| WO | 2007/137991 A1 | 12/2007 |
| WO | 2008/037801 A1 | 4/2008 |
| WO | 2013/013890 A1 | 1/2013 |
| WO | 2013/013892 A1 | 1/2013 |

OTHER PUBLICATIONS

GB Search Report, dated Mar. 13, 2013, from corresponding GB application.
Chinese Office Action issued in Application No. 201380070499.7, dated Nov. 30, 2016.

* cited by examiner

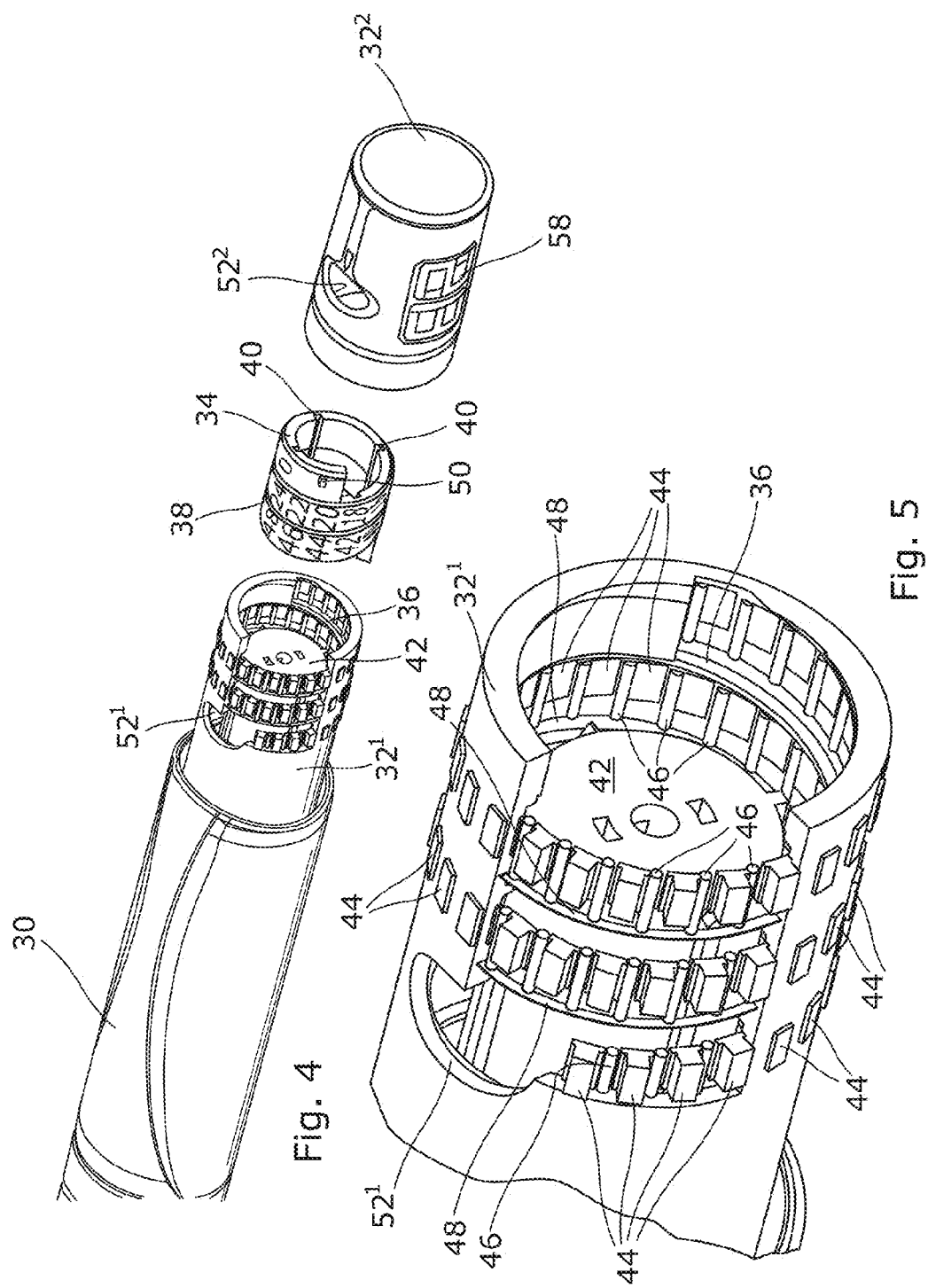

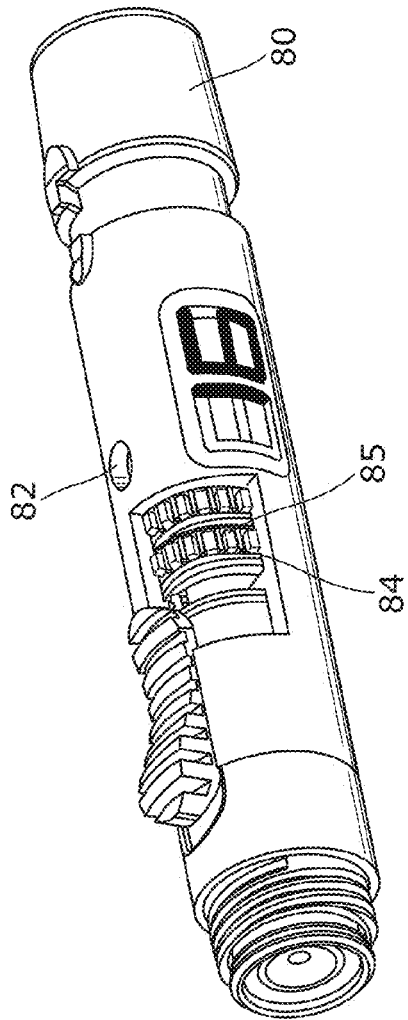
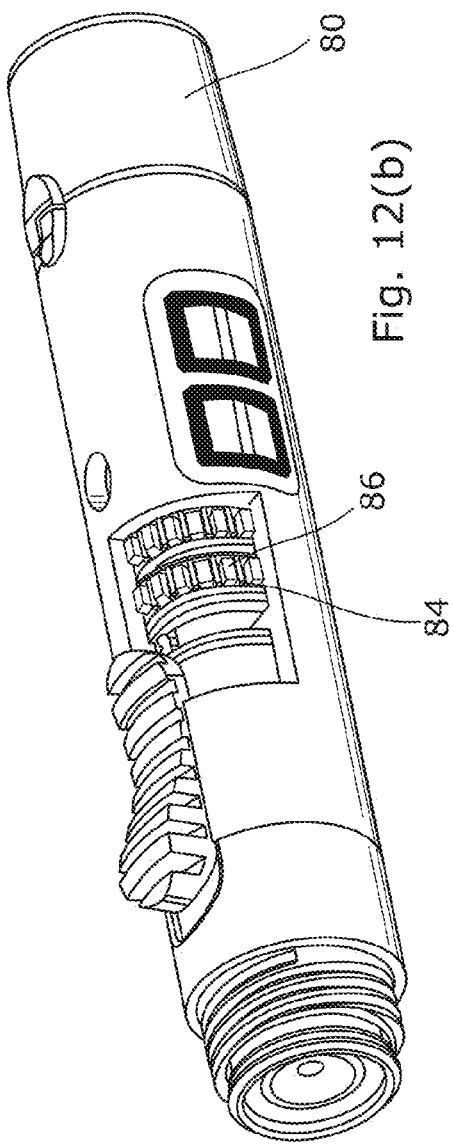
Fig. 12(a)
Fig. 12(b)

PEN-TYPE DRUG INJECTOR WITH DOSE ENCODER HAVING PIEZOELECTRIC TRANSDUCERS AND ALPHANUMERIC SEGMENTED ELECTRONIC DISPLAY THEREFOR

This invention relates to display arrangements and in particular, but not exclusively, to display arrangements incorporating an electrical display device in which the electrical power required to write an image on the display is derived from one or more transducers that respond to relative movement between two members.

Many devices use an alphanumeric or graphical display to indicate a parameter or state of a device. For example, in medical substance delivery devices, it is common to incorporate a numerical scale or the like so that a parameter of the delivery can be adjusted to a particular value according to the particular application. Thus, in our Autopen® and other automatic injector devices it is common to provide a display which indicates the magnitude of a dose that has been dialed in or otherwise set in the device. Other possibilities of parameters to be indicated include a count of the number of complete doses that have been delivered by a multiple dose device, or a graphical display representing progress and/or successful completion of a dose. Similar counts, parameters etc are displayed on other medical substance delivery devices such as aerosol or powder inhalers, and so on. The invention may of course be used for other delivery devices and indeed other applications where a variable parameter is to be displayed that depends on relative movement; there are many instances where a member is moved by a variable amount to set or dial in a particular parameter which needs to be displayed graphically, and the invention extends to such devices in general.

In existing forms of automatic injector devices, the displays tend to be in the form of a scale with the numbers printed circularly or helically around a cylindrical surface, with the numbers being read off against a mark or through a window. Because the numbers need to be packed in a relatively small space, they are inevitably small in size (typically between 2 to 4 mm in height) and these can be difficult to read in poor light conditions or by those of impaired vision. Sometimes, only even numbers are printed on the scale and setting an odd number can be confusing. Particularly where the numbers are used to set a dose, misreading can have a severe impact due to under- or over-dosing.

There is therefore a need to provide an arrangement in which the size of the display element is not constrained in this manner, so that display digits or other display elements of a larger font size can be displayed. There is also a need to provide a display which is self-powered and which changes the indicia displayed dependent on the relative position of two members.

It is known to incorporate a liquid crystal display to provide a digital read out on medical delivery devices but these have their own disadvantages; they tend to be flat and set back within the body of the device and therefore hard to see clearly and susceptible to reflections. In poorly lit or sunlight conditions they can be difficult to read due to poor contrast. They require the consumption of power to maintain the display image, and this is usually provided by a battery. This adds to the complexity of the device, and introduces potential concerns about longevity and reliability. Also, incorporation of an electrical battery in the device creates disposal problems. Furthermore, such devices rely on the circuit incorporating electronic memory and/or electronic counters.

US2005/028447 and US2006/0011651 each disclose an inhaler device in which an electronic counter arrangement provides a running count of the number of doses delivered. An electronic counter circuit adjusts the count by one in response to an electric pulse generated by e.g. a piezoelectric element that is struck each time a dose is dispensed. In these devices the electronic circuit incorporates electronic memory to keep a count and responds to successive events of identical type only (the strike caused by delivery of a dose). If the electronic circuit should suffer a momentary fault, all data will be lost.

We have designed a display technology that does not require a count to be held in an electronic memory circuit, thereby overcoming the above shortcoming. Instead the display detects the relative position between two movable members and sends to a bistable display (or other suitable display not requiring electrical energy to maintain the display between changes) a characteristic signal that varies according to the relative position of the members. In this way, even if the display were to lose the current indicated position, the next increment of movement will send the corresponding characteristic signal and so the data will not be lost. Also, preferred embodiments of the invention respond to the varying extent of movement as opposed to a repeating single event.

In a related aspect, we have designed a display technology that uses a display on which an image can be written such as, for example, an electronic paper device or other electrically addressable device, and in which the electrical energy for writing an image on the display is significantly or wholly generated internally by conversion of mechanical energy into electrical energy and which does not require the consumption of electrical energy to main a displayed image or indicia, thereby reducing or negating a requirement for external electrical power.

In one aspect, this invention provides a display system adapted to display a variable image that varies dependent on the relative position of a first member and a second member that are mounted for relative movement, said system comprising:

a transducer responsive to relative movement of said elements to output an electrical signal;

a position encoder circuit for receiving the electrical signal from said transducer and for outputting a position signal that varies according to the relative position of said members, and a display arrangement for receiving said position signal and setting on said display an image representative of the relative position of said first and second members.

Preferably, the position encoder is an absolute position encoder, rather than an incremental position encoder.

Preferably, said position encoding circuit is additionally responsive to said electrical signal from said transducer to clear the display of at least a part of a previous image before setting said image representing the current relative position. Conveniently, in response to an increment of relative movement of said first and second members, said transducer outputs an electrical signal (for example a pulse or other time varying signal), an initial portion of which is used to clear the display and a subsequent portion of which is used to set the current display. Thus, said transducer may produce an electrical signal comprising a negative voltage excursion and a positive voltage excursion.

Conveniently, said transducer comprises a piezoelectric element. Advantageously, said position encoding circuit comprises cooperating elements provided on said first member and said second member respectively. For example, said position encoding circuit may comprise a group of switches or switch contacts associated with one member, with preselected permutations of said switches being made or closed by a plurality of cooperating elements on the other member, arranged along the path of relative movement, whereby relative movement causes successive different permutations of the switches to be made.

In another aspect this invention provides a medical substance delivery device including:

a movable control member, at least one transducer responsive to movement of said control member to convert mechanical energy into electrical energy to output an electrical signal;

a drive circuit for receiving said electrical signal and for outputting an output drive signal, and a display device for receiving said output drive signal and displaying a variable image that varies consequent on said relative movement.

The display may be used in many applications where information needs to be displayed clearly to a user. Thus, where a device is adapted to deliver said substance in a dose of variable magnitude, and said control member is manually operable to set the magnitude of a dose, the display device may be operable to display an image representative of the magnitude of the set dose. The display may respond to movement of the control member in one direction only, but in other instances said control member may be moved in opposite senses to increase and decrease the set value, and the image on said display may correspondingly vary to indicate an incremented or decremented value.

In another example, said control member moves to or past a selected position during preparation or delivery of a dose, and said movement to or past said selected position is effective to energise said transducer to output an electrical signal, whereby said display device displays an image representing a delivery state of the medical substance delivery device.

In the device as defined above, a position encoder circuit measures or detects the instantaneous relative position of the members and as such does not require the use of a counter or other memory to remember the last position. This is in contrast to devices that require an electronic circuit to count pulses to deduce a position from the number of pulses counted.

In another example the device may include a plurality of transducers and, during delivery, said control member may move in proportion to the amount of medical substance delivered, with said transducers being energised in turn as said control member moves, and said display device displaying a cumulative indication of the amount of the medical substance delivered.

Various arrangements of transducer are possible. Thus a plurality of transducers may be provided, each associated with a respective conductor connected to said drive circuit, with movement of said control member causing said transducers to be energised in turn upon movement of said control member in a given direction. In one implementation, each transducer may be disposed between two adjacent conductors, being adapted to be caused to contact a selected one of said adjacent conductors dependent on the direction of movement of said control member.

In an alternative arrangement a single transducer may be provided, and the arrangement may include a plurality of conductors connected to said drive circuit, with movement of said control member in a given direction causing said transducer to apply an electrical signal to respective said conductors in turn dependent on the extent of movement of said control member.

In some arrangements the or each transducer is electrically connected to a respective said conductor.

Said display device may take a wide range of different forms; it may include a plurality of addressable picture elements adapted to display a respective indicium when a given electrical signal is applied said drive circuit. Said addressable picture elements make up a multi-segment display, for example an alpha-numeric display, or a cumulative area display, such as a bar chart or pie chart.

It is particularly preferred for said display device to be a bistable display device, so that it holds an image once written without requiring electrical energy to maintain the image, for a prolonged period, so that the device is self-powered e.g. by the conversion of mechanical energy. Preferably said display device comprises an electronic paper device or electronic ink, using technology such as is commonly used in electronic books.

The transducer may take any suitable form that converts the mechanical energy of movement into electrical energy; it may conveniently include at least one piezoelectric element.

In another aspect this invention provides a display arrangement including:

a first member and a second member arranged for relative movement in at least one direction;

a plurality of conductors spaced in said direction on one of said first and second members;

a drive circuit for receiving each of said conductors as inputs and for providing a respective output, whereby an electrical signal applied to one of said conductors causes a respective corresponding output signal;

a display for receiving said output signal and for displaying a corresponding indication, and an electrical signal generating source responsive to a given extent of change of relative position of said first and second members in a given direction to generate a signal that passes to a respective conductor dependent on the relative position of said members, thereby to display an indication of relative position.

Conveniently said electrical signal generating source comprises a transducer which moves with the other of said first and second members, and which in use is energised and caused to apply an electrical signal to said conductors in sequence as relative movement of said members occurs in a given direction.

Preferably said electrical signal generating source comprises a plurality of transducers each associated with at least one respective conductor, and said other member is adapted to energise said transducers in sequence as relative movement of the members occurs in a given direction. In one example each transducer is disposed between two adjacent conductors, and adapted to be caused to contact a selected one of said adjacent conductors dependent on the direction of relative movement of said members. In another example each transducer is hardwired to a pair of conductors.

Said display may be planar or, especially where the display is on a barrel or the like, it may include a cylindrical portion.

The relative movement detected may be circular, linear, helical or indeed along any predetermined path.

Advantageously, a refresh circuit is included for clearing elements of said display image, at least partially to reduce ghosting.

In another aspect this invention provides a parameter display arrangement for a medical substance delivery device, wherein preparation and/or operation of said device is accompanied by relative movement between two members in at least one direction, said display arrangement including:

a plurality of conductors spaced in said direction on one of said first and second members;

a drive circuit for receiving each of said conductors as inputs and for providing a respective output, whereby an electrical input signal applied to one of said conductors causes a respective corresponding output signal;

a display for receiving said output signal and for displaying a corresponding indication, and an electrical signal generating source responsive to a given extent of change in relative position of said first and second members in said direction to generate a signal that passes to a respective conductor dependent on the relative position of said members.

Preferably said electrical signal generating source comprises a transducer operable to generate an electrical signal in response to application of mechanical energy.

In yet another aspect, this invention provides a medical substance delivery device including a movable control member, a transducer responsive to movement of said control member to convert mechanical energy into an electrical signal, an absolute position encoder for receiving said electrical signal and outputting an absolute position signal dependent on the position of said control member, and a display signal for receiving said absolute position signal and displaying an image representation of the movement of the movable member.

Whilst the invention has been described above, it extends to any inventive combination or sub-combination of features set out in the following description, claims or drawings. In particular the optional features set out above may be incorporated in each of the various aspects set forth.

The invention may be performed in various ways and, by way of example only, various embodiments thereof will now be described in detail, reference being made to the accompanying drawings, in which.

Figure 3A:
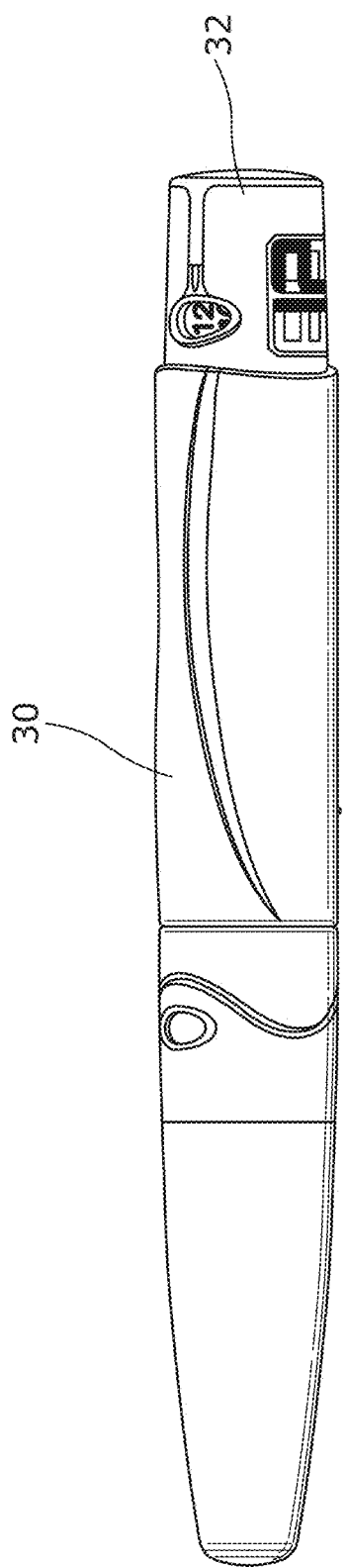
Figure 3B:
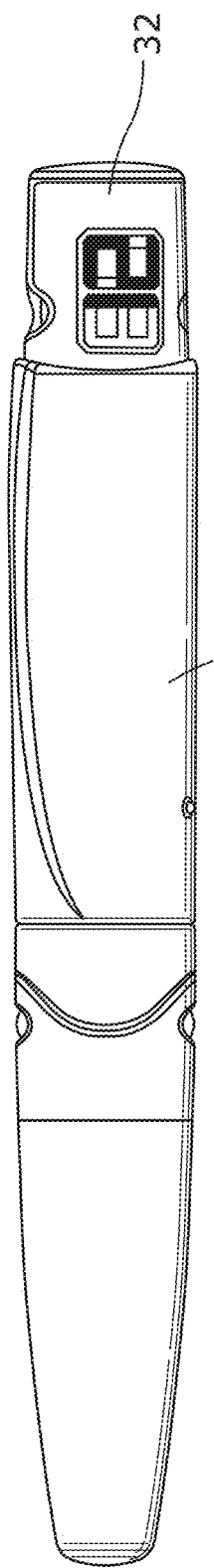
Figure 6:
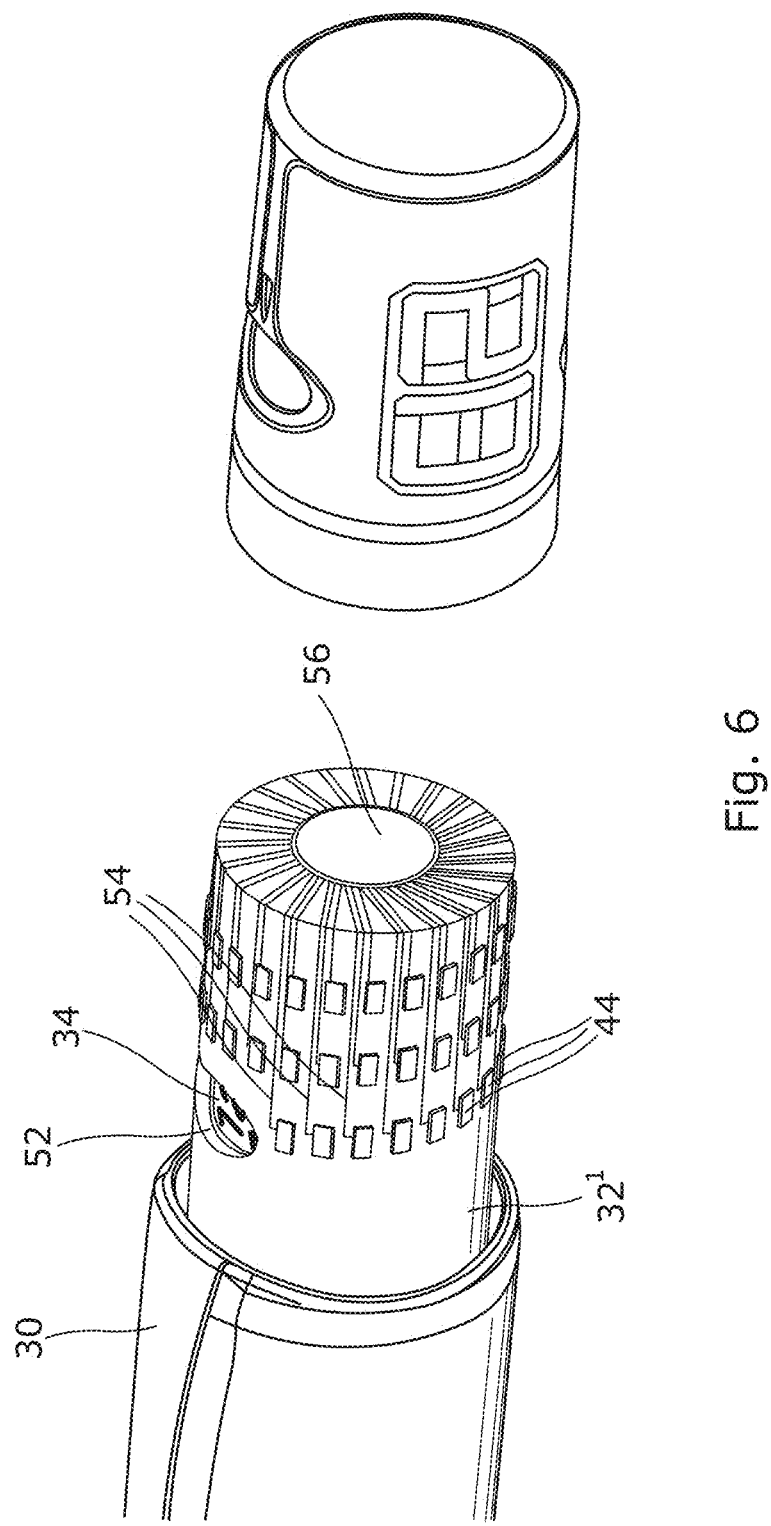
Figure 7B:
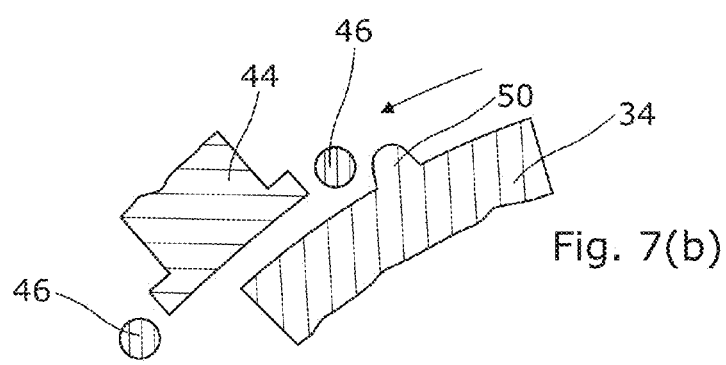
Figure 7A:
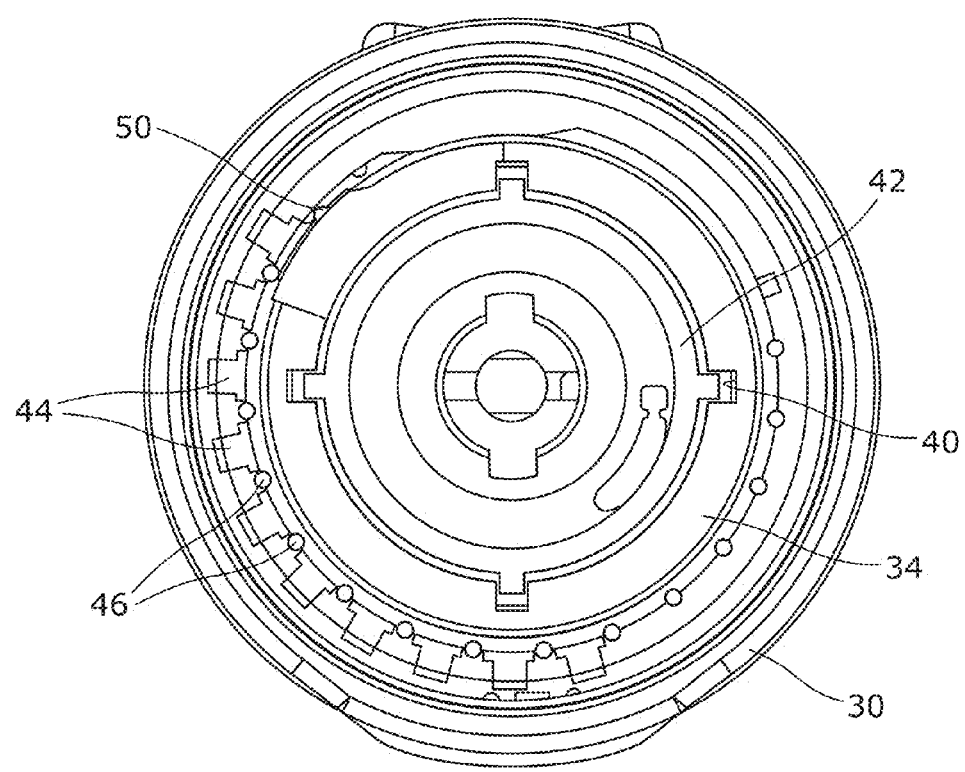
Figure 8:
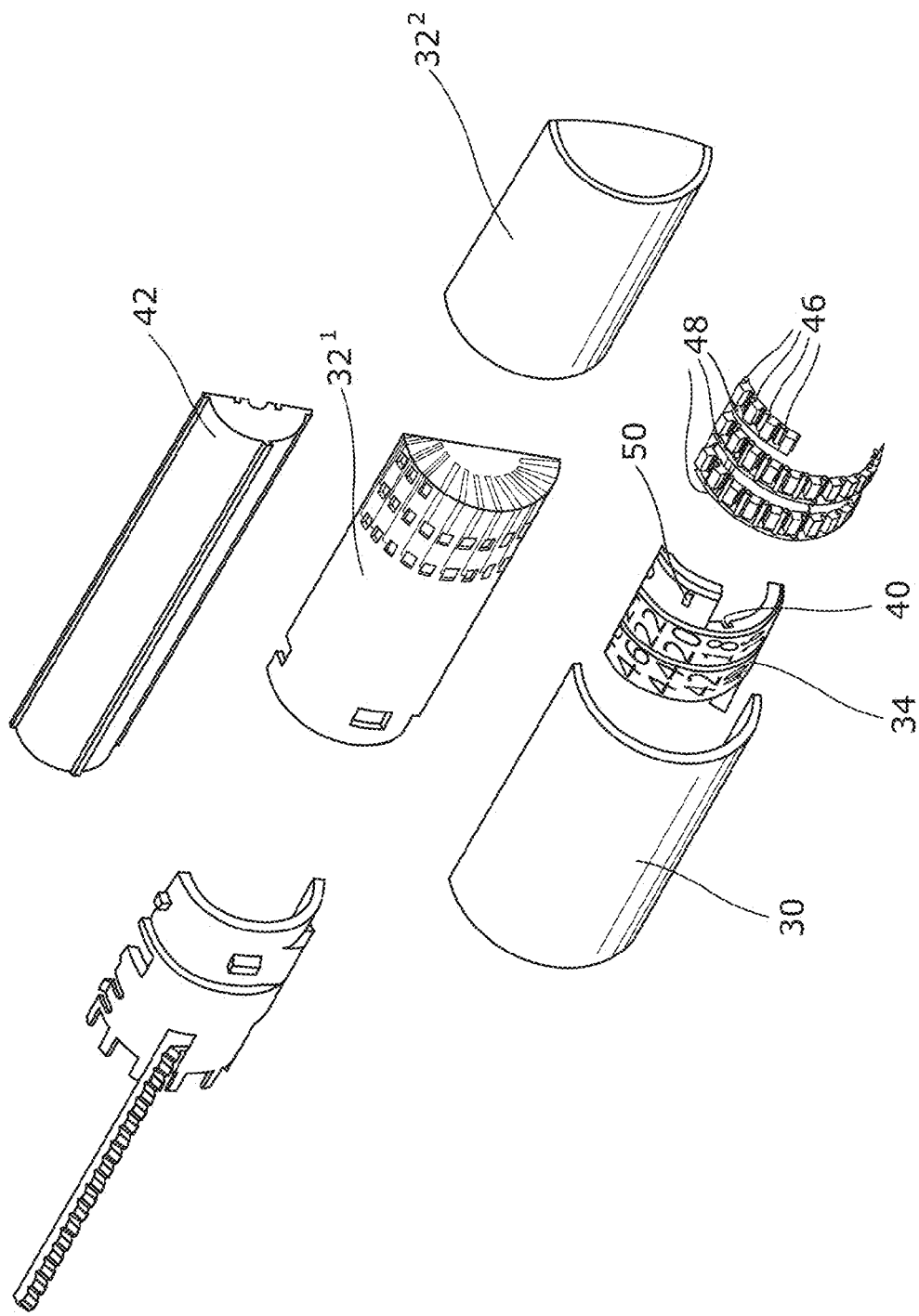
Figure 9:
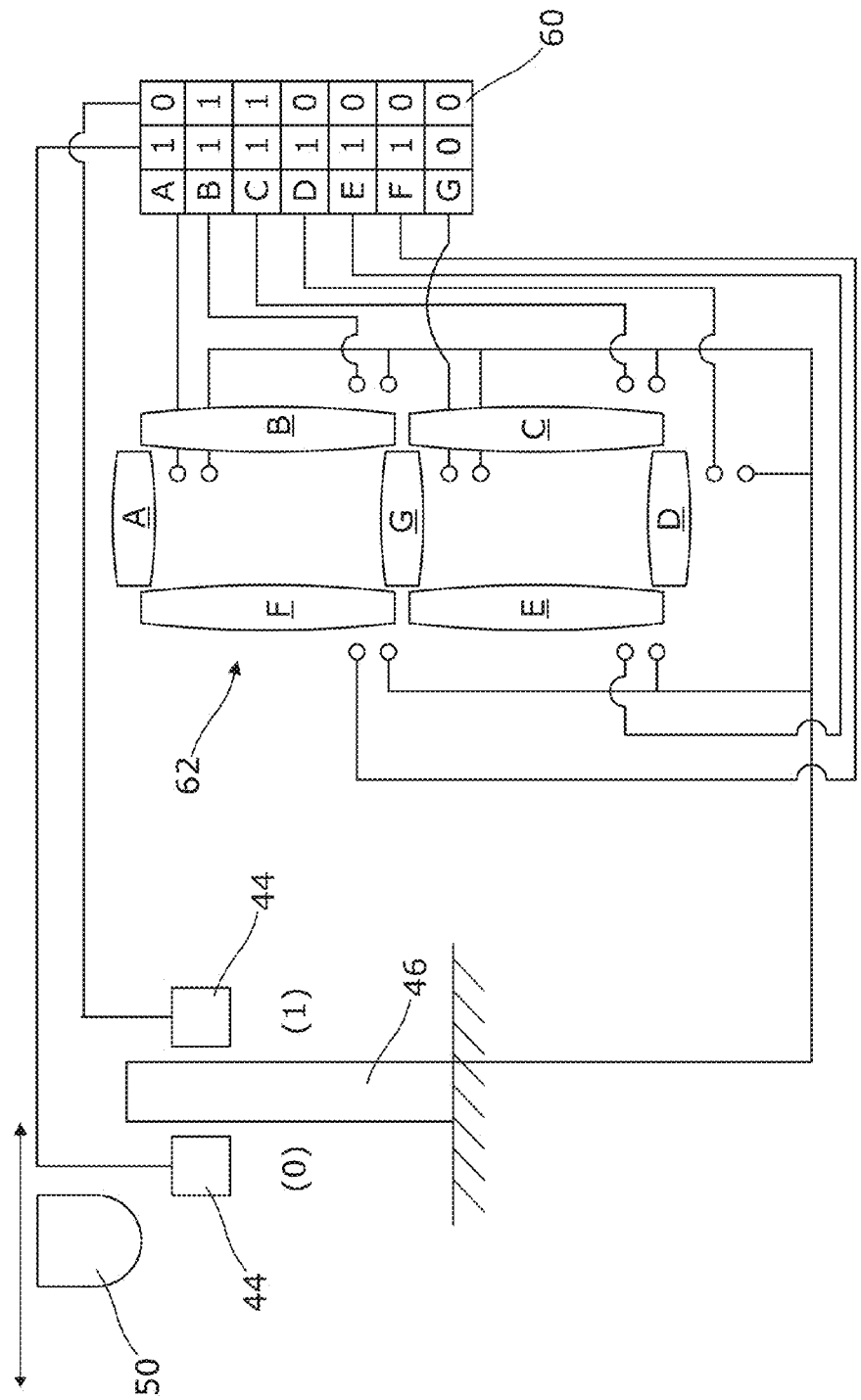
Figure 10:
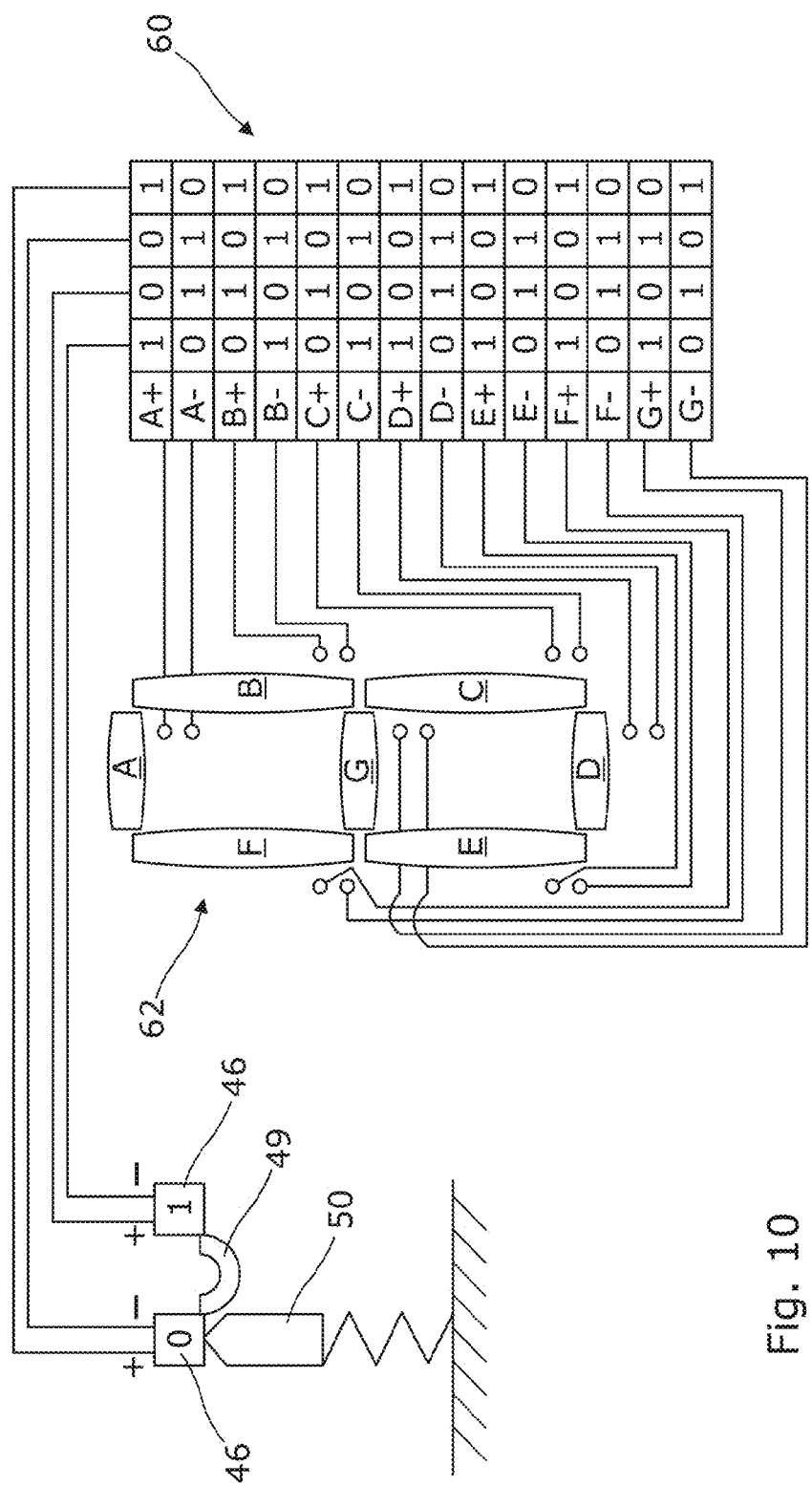

FIGS. 3 (*a*) and (*b*) are side views of an autoinjector device incorporating a dose unit display in accordance with a third embodiment of this invention to provide a digital read out of a dose set on a dose setting mechanism;

FIG. 4 is an exploded view of part of the dose setting mechanism of the autoinjector of FIGS. 3 (*a*) and (*b*);

FIG. 5 is an enlarged part cut away view of the inner portion of the dose setting knob seen in FIG. 4;

FIG. 6 is an exploded view showing the inner and outer portions of the dose setting knob prior to assembly;

FIGS. 7(*a*) and 7(*b*) are a section view and an enlarged detail view respectively showing the energising projection on the moving member about to engage and flex a piezoelectric element in engagement with an electrical contact;

FIG. 8 is an exploded view of the arrangement shown in FIGS. 3 to 7;

FIG. 9 is a circuit view showing one of the piezoelectric elements that are mounted on the inner portion of the dose setting knob, the adjacent conductor elements, and a circuit mapping the signals applied to the conductors to the relevant segments of a seven segment display;

FIG. 10 is a circuit view of an arrangement similar to that shown in FIG. 9 but showing an arrangement in which selected segments are actively written, with the remainder being actively cleared, and with multiple piezoelectric elements.

Figure 11:
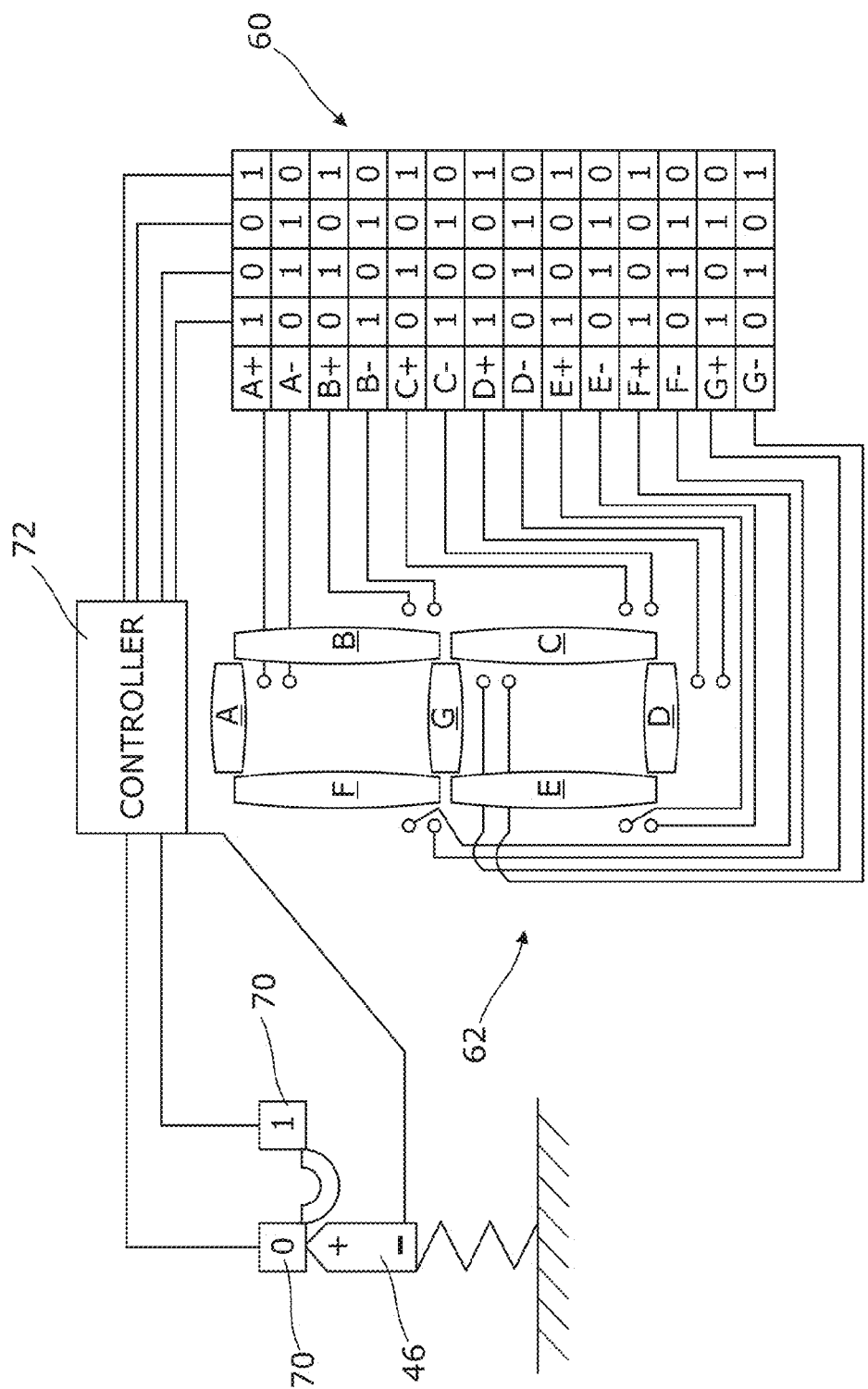
Figure 13:
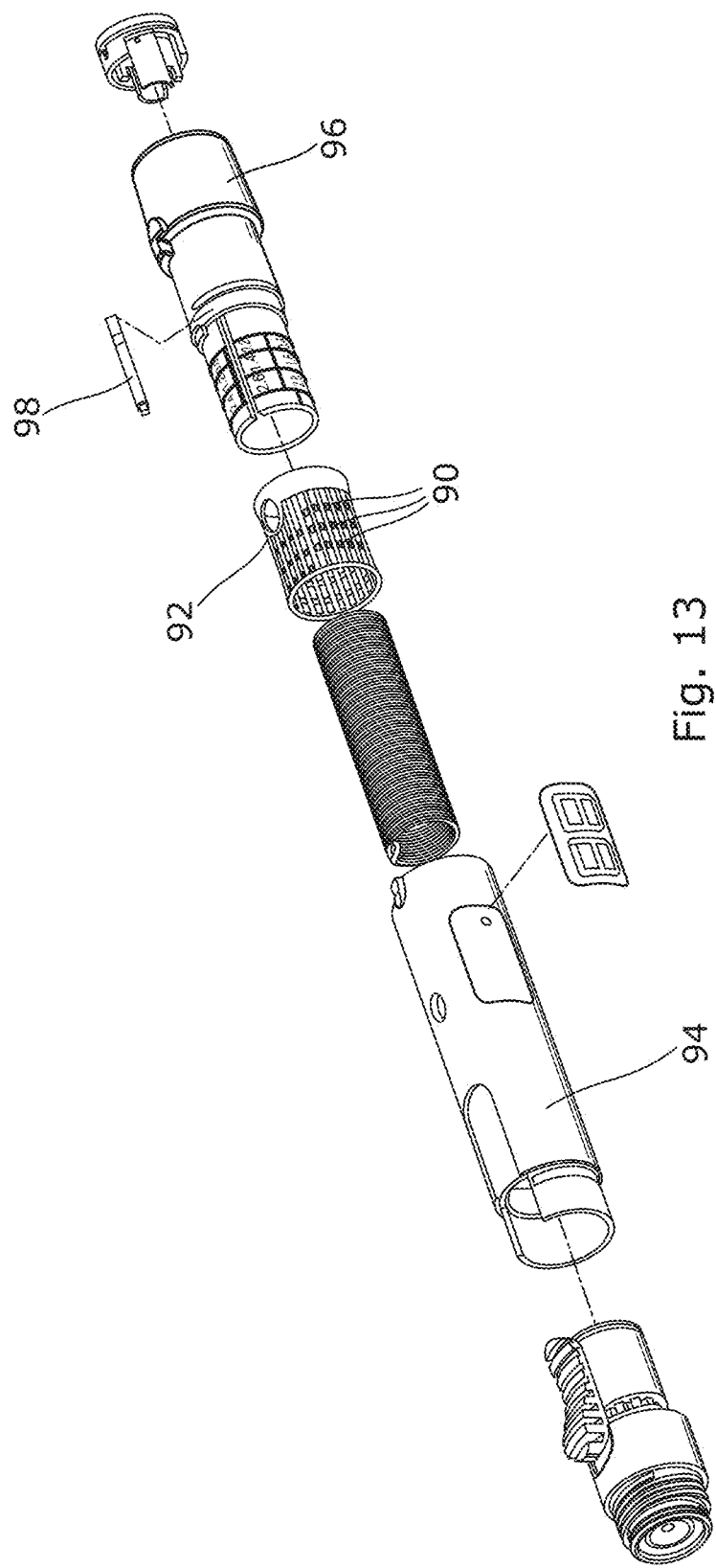
Figure 14:
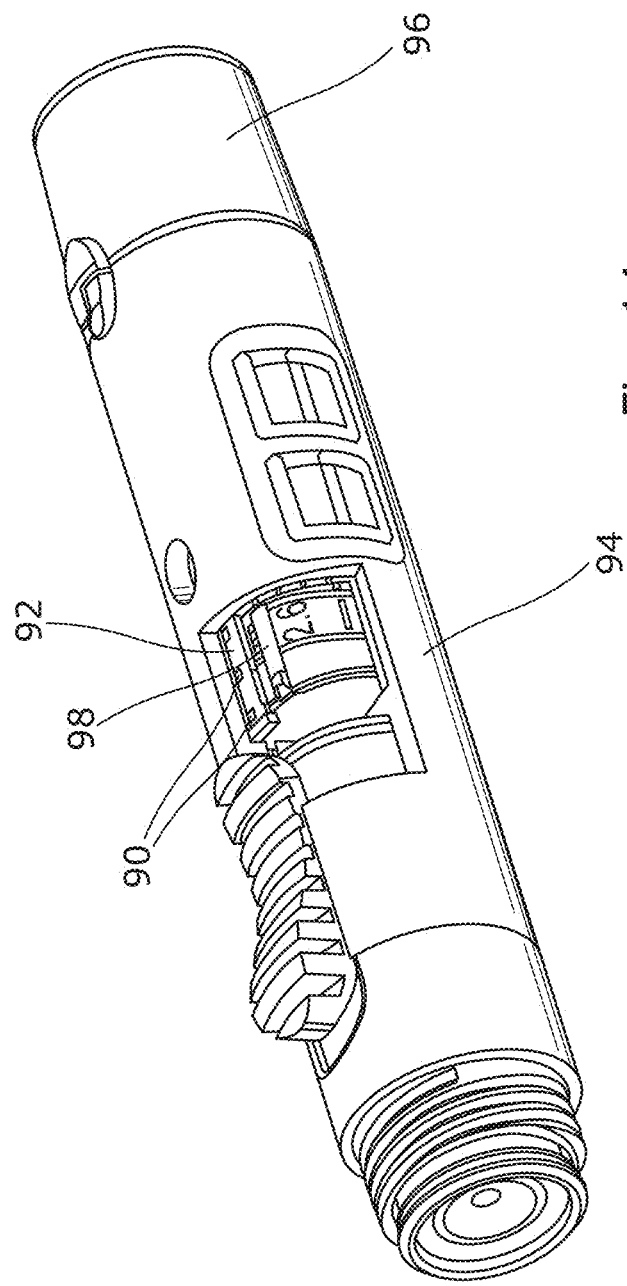
Figure 15:
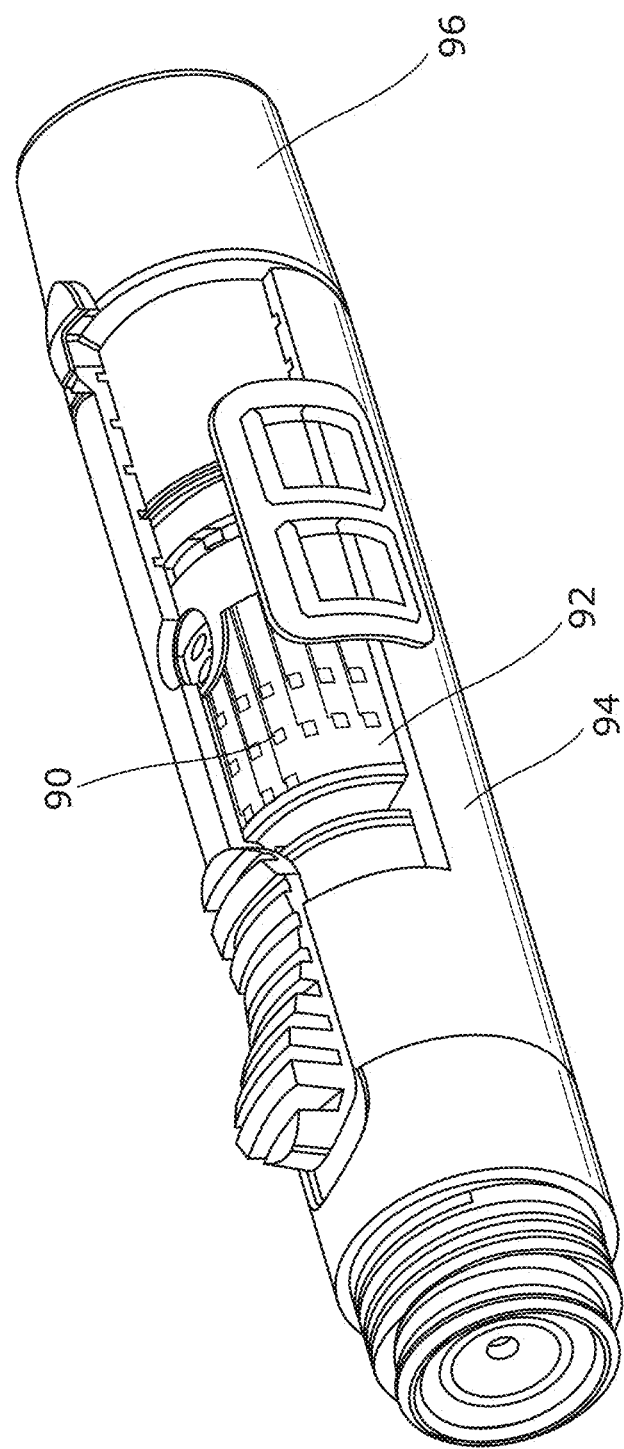
Figure 16:
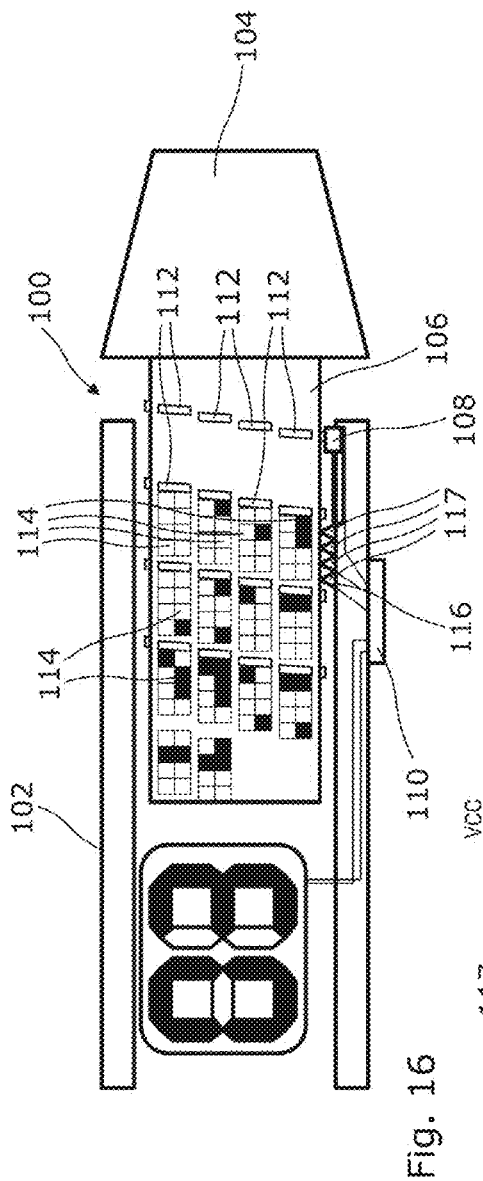
Figure 17:
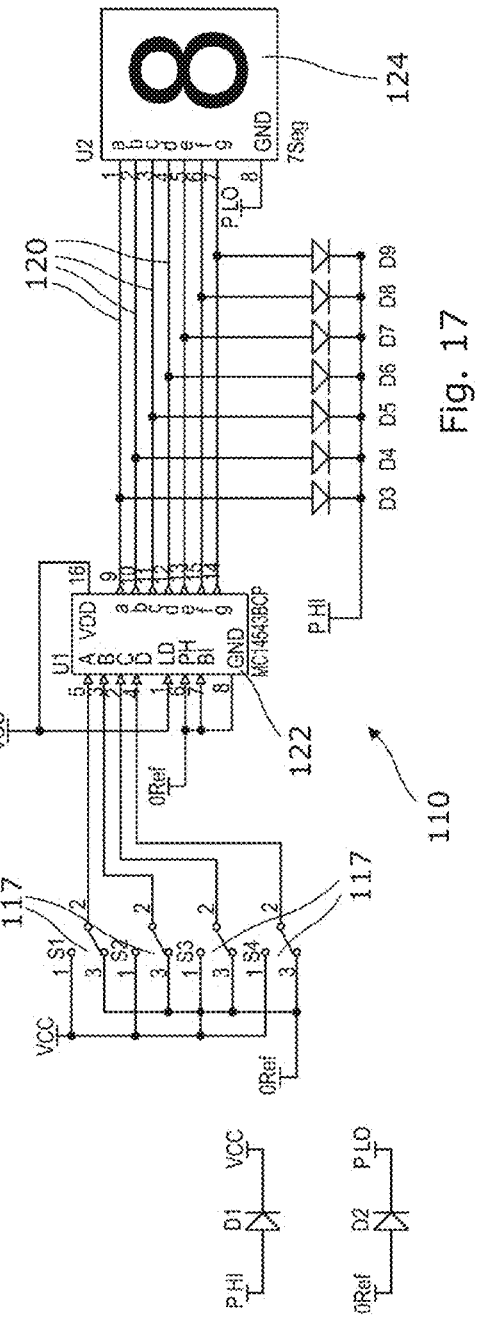

FIG. 11 is a circuit view of an arrangement similar to that shown in FIG. 10, with active writing and active clearing, but using a single piezoelectric element;

FIGS. 12(*a*) and (*b*) are part sectioned views of an autoinjector device incorporating a dose unit display in accordance with a fourth embodiment of this invention in the '00' and '16' positions respectively;

FIG. 13 is an exploded view of an autoinjector device incorporating a dose unit display in accordance with a fifth embodiment of this invention;

FIG. 14 is a part sectioned view of the autoinjector of FIG. 13, when assembled, and showing the sprung straining finger;

FIG. 15 is a view similar to FIG. 14, but showing the piezoelectric elements and conductive tracks;

FIG. 16 is a schematic view of a dose setting arrangement in accordance with a sixth embodiment of this invention, and FIG. 17 is a circuit diagram for the sixth embodiment.

Figure 1:
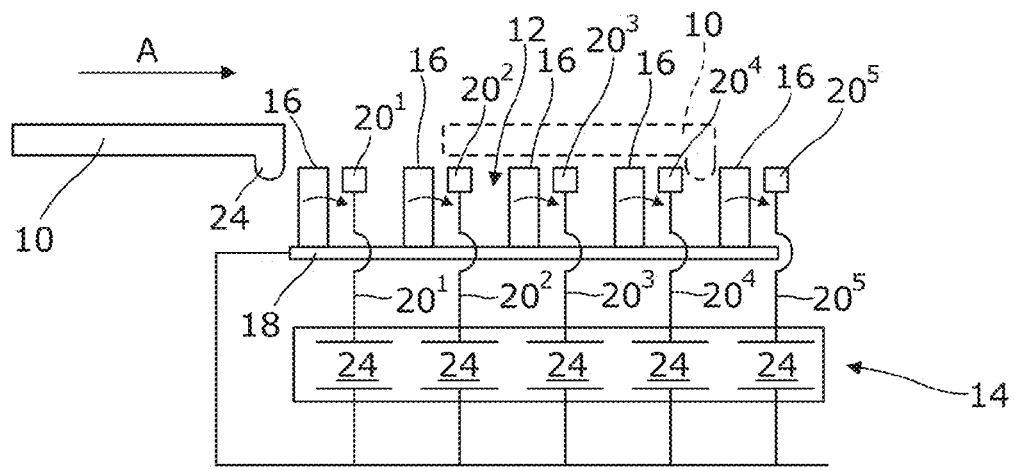
FIG. 1 is a schematic view of a first embodiment of a position display arrangement in accordance with the invention.

Referring initially to FIG. 1, the display arrangement is designed to provide a visual indication of the relative position of a moveable member 10 relative to a fixed member 12 and to display this on a display device 14 as a cumulative bar chart or "thermometer" graph 14. Disposed on the fixed member 12 is an array of spaced piezoelectric rods 16 which upstand from a common ground connection 18. Adjacent each piezoelectric element 16 is an electrical contact $20^1$ to $20^5$ each with a lead $22^1$ to $22^5$ which passes to the display 14.

The moveable member 10 in this example is constrained to move along a linear path as indicated by the arrow A in FIG. 1. Projecting from the forward end of the moveable member 10 is a projection 24 which is disposed so that, as the moveable member 10 moves to the right in FIG. 1 it engages the first piezoelectric element 16 and bends it towards and into contact with adjacent conductor contact $20^1$, and successively contacts and bends the other rods 16 in the sequence as the moveable member moved along its path. In bending the piezoelectric rods 16, a potential difference is created which, when the rod 16 closes against the contact 20, is applied across a cell 24 of the display 14. In this embodiment, the display has a number of bar segments that are energised by the voltage applied to leads $22^1$ to $22^5$. As the moveable member 10 moves to the right, it will successively engage, strain and then release the piezoelectric rods 16 so that the cells 24 of the display 14 will be successively energised thereby cumulatively indicating the relative position of the moveable member 10 relative to the fixed member. The cells of the display are made up by respective pairs of electrodes, one of which being connected to ground 18 and the other being connected to a respective lead $22^1$ to $22^5$.

The display may be a display in which a cell is written electronically, changing colour from e.g. white to black as it is written, and preferably retaining this state when the applied voltage is removed. In this particular example the display is a bistable display, in which the cells change from a default white to black when the piezoelectric voltage is applied and retain the black setting thereafter.

This embodiment determines the relative position of the two members by using the series of piezoelectric elements as transducers converting mechanical energy into electrical energy to switch the state of the cells to write an image. As noted, the display is bistable and so no external power is required to maintain the state of the cells when they have been switched. The image displayed is changed by an object moving along a path and successively energising transducers spaced along that path. The display is directly driven by the position of the object.

This may be used in a wide range of different applications for example, in a medical delivery device to indicate the progress of delivery of the medical substance, a dose set amount, or any other parameter that can be determined based on the relative movement of two members.

Figure 2:
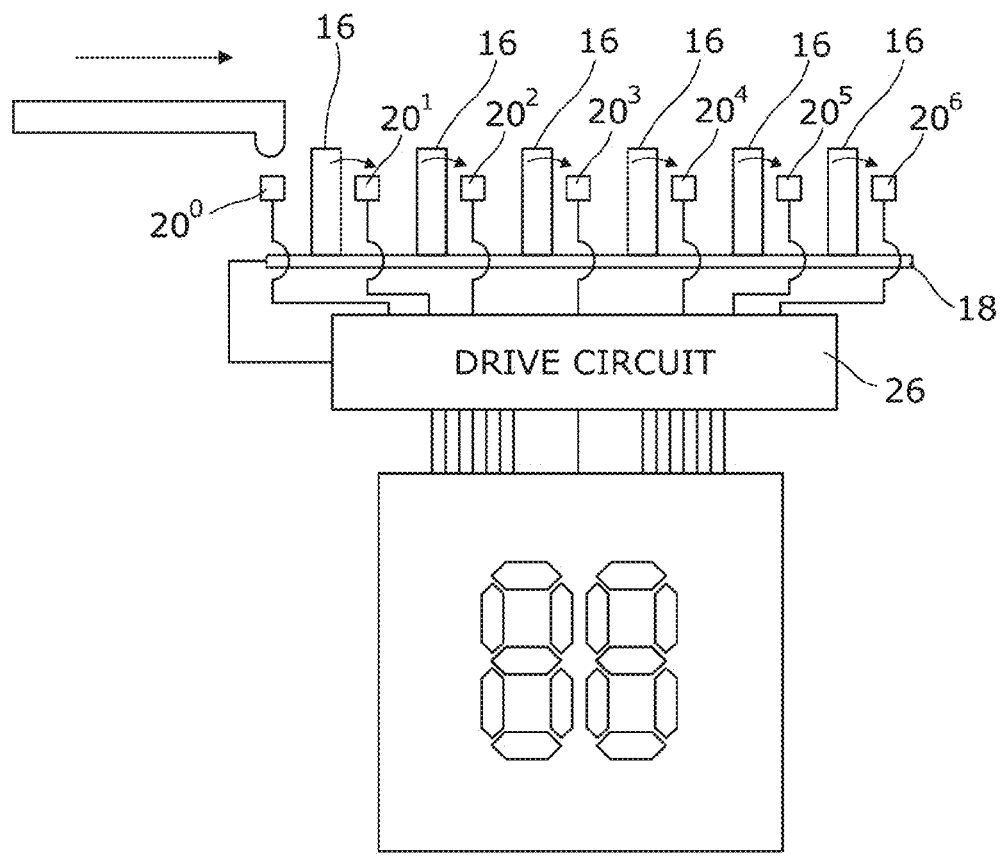
FIG. 2 is a schematic view of a second embodiment of a position display arrangement in accordance with the invention.

Referring now to FIG. 2, in this embodiment, the principle of using a series of piezoelectric elements to provide a self powered display is extended to an arrangement which allows a numerical count to be incremented or decremented according to the position of two relatively moveable members.

As seen in the arrangement of FIG. 2, a moveable member 10 is provided with a projection 24 as before. In this arrangement, the piezoelectric rods 16 are again attached to a common ground 18 which passes to a display driver circuit 26. Each piezoelectric rod 16 is disposed between two contacts 20 and can be deflected to the right to close with the right hand contact or, in the opposite direction, to close with the left hand contact depending on the direction of movement of the moveable member. Each of the contacts 20 therefore corresponds to a count number. The contacts are connected by the leads to the driver circuit 26 which codes or maps each contact to a digit in a bistable alphanumeric display. In operation, as the moveable member moves to the right, it successively engages strains and causes the piezoelectric rods 16 to close with the adjacent right hand contact and so as the moveable member moves, the piezoelectric rods 16 will apply voltage successively to the contacts $20^1$ to $20^6$. The voltages appearing on the lines $20^1$ to $20^6$ pass to the drive circuit which maps the signal on a contact to the appropriate segments corresponding to digits 1 to 6 in sequence. If the moveable member 10 is moved in the opposite sense it causes the piezoelectric rod to the left of the projection to be deflected and then to close with the contact to the left of the piezoelectric rod, thereby energising the segments corresponding to the next member down.

In each of these embodiments, the preferred display is an electronic paper display using any suitable e-paper or e-ink technology examples of which are well know to those skilled in the art. As noted in the above description, the display may be alphanumeric or it may be graphical or a mixture of both. The second embodiment may also include an arrangement for refreshing the seven segment display before each new digit is written. This may be provided by means of a further piezoelectric element (not shown) which applies a reverse voltage to all of the segments immediately prior to writing the respective segments for the next selected digit. Alternatively, as to be described in more detail below, the drive circuit may map each input to both write the required segments making up the new digit, whilst also clearing the other segments.

Referring now to FIGS. 3 to 7, there is shown an auto-injector device that is a development of the device shown in our co-pending application WO2011/045611. Reference is directed to that specification for a description of the internal operation and dose setting mechanism. For present purposes all that is required is to note that there is a main body 30 from the rear end of which projects a dose setting knob 32. The dose setting knob 32 is mounted for rotation on the rear end of the device and moveable axially between a dose setting position in which the knob may be rotated to dial up a dose, and a firing position in which the knob is constrained against rotation whilst the dose is delivered.

During a dose setting routine, with the main body held stationary, the user rotates the dose setting knob relative to an internal scale 34 of helical form (see FIG. 4). The scale is threadedly engaged with the dose setting knob 32 so that, as the dose setting knob 32 is rotated relative to the scale 34 and the main body 30, the scale shifts axially as it climbs the thread. When the required dose has been set, the device is fired and, as a consequence of firing, the scale 34 rotates back to the zero setting.

Turning now to FIG. 4, the dose setting knob is formed of an inner portion $32^1$ and an outer portion $32^2$. The inner portion $32^1$ carries on its inner surface, a thread form 36 that engages a helical groove 38 on the outside of the scale 34. The scale carries four equispaced internal splines 36 that allow it to rotate with, but move axially relative to, a splined drive shaft 42.

As can be seen in FIG. 5, the inner portion $32^1$ of the dose knob has a plurality of positive contacts 44 arranged in a helical array in apertures within the inner cap portion at a pitch corresponding to that of the numerical digits on the outside of the scale and at half the angular spacing (as the scale members are even only). Spaced alternately with the positive contacts is a plurality of piezoelectric elements 46 which connect at respective one ends to a common negative or ground connection passing 48 helically adjacent but spaced from the series of positive connections 44. Each piezoelectric element 46 is spaced from the positive connections 44 to either side, and also projects radially inwardly of the contacts as can be seen in FIGS. 7($a$) and 7($b$). The scale 34 has at its rear end a radially projecting tooth 50 (see FIG. 7($a$)) designed so that it successively strains the piezoelectric elements that lie in its path as the inner dose knob portion $32^1$ rotates relative to it.

When assembled, and with the scale 34 at its zero position, with the number zero on the end of the scale underlying the viewing window $52^1$ on the inner cap portion $32^1$, the tooth 50 lies under the first positive connection 44 in the series (referred to as (0) positive connection). In use, as the dose setting knob 32 is rotated relative to the scale 34 in a clockwise direction viewed from the rear end, the projecting tooth 50 will ride over the back of the first piezoelectric element 46 straining it counter clockwise, with a potential difference appearing across the piezoelectric element, until the piezoelectric element makes electrical contact with the (1) positive connection 44. Likewise, continued turning of the dose setting knob 32 will successively strain and close the next piezoelectric element 46 against the next counter clockwise positive connection 44 in the series, and then returning to its equilibrium position as the tooth 50 snaps past it.

If the dose setting knob 32 is rotated in the opposite, counter clockwise direction, then the piezoelectric elements will be strained by contact with the tooth in the clockwise direction, thus making contact with the clockwise adjacent positive connection 44. In this manner, rotating the dose setting knob in either direction causes a potential difference to be applied to a succession of positive connections in the counter clockwise direction if the dose is being increased, and to a succession of positive connections in the clockwise direction if the dose is being reduced.

Referring now to FIG. 6, each positive connection 44 is connected to a respective conductive track 54 that runs axially to the end wall of the inner portion and then generally radially to a chip on board (COB) 56 which receives each track and maps it to the appropriate segments of a two digit seven segment display. In this embodiment, the seven segment display is formed as an electronic paper display device 58 mounted on the side of the outer portion of the dose setting knob, with the outputs from the COB 56 being suitably being routed to the display.

In operation, as a dose is dialed in by rotating the dose setting knob, the projecting tooth on the scale energises successive piezoelectric elements which in turn apply a potential difference across a unique conductor and that signal is mapped or decoded to drive the electronic display.

Referring now to FIG. 9, there is shown a schematic view of the first piezoelectric element 46 and the (0) positive connection and (1) positive connection 44 connected to a drive circuit 60 set up to drive a seven segment display 62 on the electronic paper display device 58. In this arrangement, moving the piezoelectric element to the left will cause a potential difference to be created which is mapped and passed by the drive circuit 60 to apply a potential difference across the six segments making up the "0" digit, as seen in the first column of the mapping matrix applied by the COB 56. Moving the piezoelectric element 46 to the right causes it to create a potential difference which is passed to the right hand contact which is converted by the second column of the matrix to energise the two segments making up the '1' digit. As explained above, a movable element has a tooth 50 that successively engages the piezoelectric elements.

Whilst in the above embodiment there is a piezoelectric element and a contact for each detectable increment of movement, with a single projection 50 successively striking the piezoelectric elements as the dose setting knob is rotated, it would be possible instead to have a single piezoelectric element which is repeatedly struck by an array of projections on the relatively stationary member, with the piezoelectric element caused to be in contact with a respective conductor from an array adjacent the projections when strained.

Depending on the particular display technology employed, a refresh step may be implemented immediately before setting each digit (or display mark) is enabled.

It will be appreciated that the above embodiment is just one way in which a self-powered position detecting arrangement may be used in a medical delivery device. Other uses include displaying the progress or completion of delivery. For example, where the medical substance being delivered is expelled by movement of a plunger, the linear or rotary position of the plunger may be detected using piezoelectric transducers driving a suitable bistable display device. The display arrangement may also be used with a suitable mechanical or electronic counter arrangement to display a count of the doses that have been delivered by a multi-use device.

The device may be adapted for any setting action which in member is moved along a predetermined path, whether rotary, helical, linear or other.

In the above embodiments, the picture elements in the display are written positively but in some instances it will be necessary to clear previously written picture elements. Thus, for example, in a seven segment display, changing from a display of '0' to '1' requires clearing of four of the segments used for 0 (i.e. those making up the strokes that provide the top and bottom vertical left hand strokes and the upper and lower horizontal strokes). This may be done by means of a separate piezoelectric transducer that clears all the segments prior to writing the next image, but, in the embodiments below, the drive circuit provides a matrix which maps each input signal to a digit and, in doing so, actively writes the segments making up the character and actively clears the segments not required.

Thus, referring to FIG. 10, in this arrangement a piezoelectric element 46 is associated with each position increment as previously. However, in this configuration each piezoelectric element 46 is hardwired to respective positive and negative tracks that pass to a drive circuit 60. The drive circuit 60 provides a distribution matrix which ensures that the relevant segments of the seven segment display are energised when the appropriate piezoelectric element 46 is strained by a sprung straining finger 50. In this arrangement, the voltage from each piezoelectric element 46 is supplied to two columns of the matrix along respective positive and negative tracks. The columns are the inverse of each other. The rows of the distribution matrix pass to corresponding terminals driving the segments of the display 62.

As previously, the piezoelectric elements 46 are arranged in a track corresponding to the movement of a moveable member relative to a fixed member. Intermediate each pair of piezoelectric elements is an insulating rib element 49. Thus, as the array of piezoelectric elements 46 moves relative to the sprung straining finger 50, the sprung straining finger is brought into engagement with and strains each of the piezoelectric elements in turn. When the sprung straining finger moves to engage and strain the piezoelectric element 46 corresponding to a zero, the positive track is applied to segment terminals A+, B+, C+, D+, E+, F+ and G−. Likewise the negative track is applied to segment terminals in inverse fashion so is supplied to A− to F− and to G+. This means that, with the positive voltage being applied to the A+ to F+ terminals, the segments A to F are written; in the case of G, however, the voltage is applied to the negative terminal and so the G segment will be actively cleared, so that the numeral 0 is displayed. When the array of piezoelectric elements 46 moves to the left as seen in the Figure, the straining finger 50 will engage and strain the piezoelectric element 46 at position 1. Here the positive track will be applied to B+ and C+ but to the negative terminals of A, D, E F and G, and the negative track will be applied inversely, thereby actively writing segments B and C whilst actively clearing segments A and D to G to provide the segments making up '1'.

The above arrangement requires a piezoelectric element 46 to be provided at each positional increment along the track of movement.

Turning now to FIG. 11, in this arrangement a series of electrical contacts 70 is disposed along the path of movement of the moveable member and a single piezoelectric element 46 is associated with the fixed member and biased towards engagement with the array of contacts. In use, as the members move relative to each other, the biased piezoelectric element 46 moves over an insulating rib element 49 and into engagement with a contact. When the piezoelectric element 46 engages a contact, a voltage signal is developed across the piezoelectric element 46 which passes along a respective track to a controller 72. The controller applies the voltage across a pair of output tracks that correspond to the particular contact 70 receiving the electrical output of the piezoelectric element 46. These tracks are supplied to the drive circuit 60 that applies a distribution matrix to apply positive and negative potential differences, to write and clear the appropriate segments as previously.

FIG. 12, there is illustrated the drive unit of a pen type injector such as our Autopen® 2 injection device. In use, this device is used in a similar manner to the embodiment of FIGS. 3-8, by rotating a dose setting knob 80 at the rear end of the device to dial in a selected number of units for the dose to be delivered. The units are displayed by means of a helical scale (not shown) that rotates with the dose setting knob and which is visible through a viewing aperture 82. In this arrangement, there is an array of piezoelectric rods 84 connected at one end to a common ground connector 86 and disposed helically consistent with the helical path of movement of the dose setting knob. The array of piezoelectric elements is interspersed with positive conductors 88, and both the piezoelectric element and the positive conductors are fixed relative to the main body of the device. In use, a radial projection (not shown) associated with the scale successively strains the piezoelectric rods and urges them into contact with the positive connectors which then causes the display to increment in a manner similar to that described above. The layout and operation is similar to that show in FIGS. 5 and 9 above.

Referring now to FIG. 13 this shows an exploded view of a sixth embodiment in accordance with this invention. As previously, a helical array of piezoelectric elements 90 is disposed on a cylindrical shell 92 that is secured to the main body portion 94. A dose setting knob 96 has a sprung element 98 that progressively strains the piezoelectric elements as a dose is dialed in. In this arrangement, the circuit of FIG. 10 may be adopted whereby each piezoelectric element 90 is connected to the display device by two tracks, with the drive circuit actively writing and actively clearing segments as necessary. Alternatively, the helical array of piezoelectric elements 90 may be replaced by a helical array of contacts, and the sprung element 98 may be replaced by a single piezoelectric element which, as the knob is rotated, is strained by engaging the next one of the contacts, successively applies a voltage across respective lines to a controller 72 as in FIG. 11, to display the position numerically.

Referring now to FIG. 16, there is shown a sixth embodiment of position sensing arrangement in accordance with this invention, applied to detect and display the position of a rotary knob that moves along a helical path, for example to set a dose. The dose setting knob 100 is mounted for threaded movement relative to a housing 102. The dose setting knob 100 has an externally grippable head 104 and a generally cylindrical body 106. Positioned inwardly of the housing 102 is a single piezoelectric element 108 connected to a position encoding logic circuit 110 which is illustrated in detail in FIG. 17 and will be described in more detail below. The cylindrical body 106 of the dose setting knob 100 is provided with a helical array of raised tabs 112 which, as the knob is rotated, successively strain and release the piezoelectric element 108 to cause movement firstly in one direction and then the other to provide a voltage swing first in one direction and then the other, as to be described below. Also provided on the cylindrical body 106 is a helical array of binary code patches 114, each patch comprising two rows each of four binary digits. In this particular example, the binary patches code for binary digits (0000;00000) to (0010; 0011) which correspond to 0 . . . 23 in decimal. The binary codes are read by a reader 116 having detectors for each of the 8 binary digit bit positions. In this particular example, the bit position detectors comprise two banks of four switches 117 which are selectively closed by the binary code patches. Thus, in FIG. 16, the blacked out bit positions may correspond to projections which close a corresponding microswitch 117 in the reader 116. It should be appreciated that there are many other ways of reading the position; for example, the binary code patches on the body of the dose setting knob may comprise conductive panels in the blacked out bit positions of the binary code patch, and the position detector may comprise a pair of sweeping contacts at each bit position, which are electrically bridged when contacted by a conductive panel at a bit position of the binary code patch. The arrangement therefore provides a unique binary code representing the angular position dose setting knob and as such operates as an absolute position encoder encoding the relative position of two objects.

Referring now to FIG. 17, the position encoder circuit 110 is shown for a single digit of the display only. The circuit is designed to make use of the feature that, as the piezoelectric element 108 is strained by and released by a tab 112 it generates a voltage swing in one direction when strained and a voltage swing in the opposition direction when the strain is released. In this arrangement, the voltage at one side of the piezoelectric element is labelled P Hi and at the other side to P Lo. When the piezoelectric element is initially engaged by a tab 112, P Hi swings low relative to P Lo.

The four switches 117 making up the reader 116 are connected to a binary decoder 122 which outputs drive voltages to a display 124. An example of a typical binary decoder is a MC14543B decoder from ON semiconductor, although any other suitable circuit may be used. The ground contact of the display 124 is connected to P Lo. A series of diodes D3 to D9 connect respective digital segment driver lines 120 to a rail at P Hi and allow current to flow when P Hi<P Lo. P Hi is also connected by diode D1 to VCC, with VCC providing a positive voltage for the decoder. 0 REF is connected to P Lo through a diode D2, providing a ground reference for the decoder. VCC and 0 Ref are only functional (and thus the decoder is only active) when P Hi is greater than P Lo. If the display has more than one digit then the right hand part of the circuit including the decoder needs to be replicated for each digit.

In operation, as the dose setting knob 104 is rotated by one setting increment, one of the raised tabs 112 on the dose setting body 106 deflects the piezoelectric element 108, causing P Hi to swing negatively relative to P Lo. The diodes D3 to D9 allow charge to flow across the display to cause all the segments of the display 124 to clear. The next binary code patch 114 engages with the corresponding binary code reader 116 and sets the switches 117 accordingly before the piezoelectric element is disengaged from the tab 112. As the piezoelectric element releases from its deflected state P Hi swings positively relative to P Lo, thus establishing VCC and 0 Ref and making the decoder active. Depending on the state of each of the switches 117 on the binary code patch 114, the switches outputs will be VCC or 0 Ref. These outputs are provided to the decoder 112 which outputs on the segment driver lines 120 the appropriate signals to cause the corresponding segments to be energised to display the decimal digit encoded by the binary code patch currently in reading alignment with the binary code detector.

Thus, as the dose setting knob is moved by an increment in either direction, the circuit of FIG. 17 will initially provide a clearing pulse that clears all segments of the display followed by a writing pulse which writes the required segments corresponding to the current position.

Although the above embodiments make use of piezoelectric elements, it will be appreciated that any other suitable transducer that converts the mechanical energy caused by movement of an object into an electrical signal sufficient to drive a display may be used.

The invention claimed is:

1. A medical substance delivery device display system adapted to display a variable image that varies dependent on the relative position of a first member and a second member that are mounted for relative movement, said system comprising:

a transducer responsive to relative movement of said members to generate an electrical signal;
an absolute position encoder circuit for receiving the electrical signal from said transducer and for outputting an absolute position encoding output signal that varies according to the relative position of said members,
wherein said absolute position encoder circuit comprises cooperating elements provided on said first member and said second member respectively, and a group of switches associated with one of said first and second members, with preselected permutations of said switches being made or closed by at least one cooperating element on the other of said first and second members, arranged along the path of relative movement, and wherein relative movement causes successive different permutations of the switches to be made; and
a display arrangement for receiving said absolute position encoding output signal and setting on a display device an image representative of the relative position of said first and second members, wherein said display device is adapted to hold a displayed image between changes without requiring electrical energy to maintain the displayed image.

2. A display system according to claim 1, wherein said position encoding circuit is additionally responsive to said electrical signal from said transducer to clear the display of at least a part of a previous image before setting said image representing the current relative position.

3. A display system according to claim 2, wherein in response to a predetermined increment of relative movement of said first and second members, said transducer outputs an electrical signal, an initial portion of which is used to clear the display and a subsequent portion of which is used to set the current display.

4. A display system according to claim 3, wherein said transducer produces an electrical signal comprising a negative voltage excursion and a positive voltage excursion.

5. A display system according to claim 1, wherein said transducer comprises a piezoelectric element.

6. A medical substance delivery device according to claim 1, wherein said display device is a bistable display device, electrical power required to write an image on the bistable display device being derived from said transducer responding to the relative movement between the first and second members.

7. A medical substance delivery device comprising:
a movable control member;
at least one transducer responsive to movement of said control member along a path to convert mechanical energy into electrical energy to output an electrical signal;
a drive circuit for receiving said electrical signal and for outputting an output drive signal that varies according to the extent of movement of said control member, said drive circuit comprising a plurality of conductors spaced along said path for successively receiving an electrical signal on said movement; and
a display device for receiving said output drive signal and displaying a variable image that varies consequent on said movement,
wherein said control member moves to or past a selected position during preparation or delivery of a dose, and said movement to or past said selected position is effective to deflect said at least one transducer to convert mechanical energy of movement into electrical energy to output an output drive signal, and
wherein said display device displays an image representing an operational state of the medical substance delivery device, said display device being adapted to hold a displayed image between changes without requiring electrical energy to maintain the displayed image.

8. A medical substance delivery device according to claim 7, wherein said medical substance delivery device is adapted to deliver said substance in a dose of variable magnitude, wherein said control member is manually operable to set the magnitude of a dose, and the display device is operable to display an image representative of the magnitude of the set dose.

9. A medical substance delivery device according to claim 8, wherein said control member may be moved in opposite directions to increase and decrease the set magnitude, and the image on said display correspondingly varies to indicate an incremented or decremented value.

10. A medical substance delivery device according to claim 7, having a single transducer, and the arrangement includes a plurality of said conductors, and movement of said control member in a given direction causes an electrical signal derived from said transducer to be applied to respective said conductors dependent on the extent of movement of said control member.

11. A medical substance delivery device according to claim 7, wherein each of at least one transducer is electrically connected to a respective conductor.

12. A medical substance delivery device according to claim 7, wherein said display device includes a plurality of picture elements adapted to display a respective one of a plurality of indicia when a given electrical signal is applied said drive circuit.

13. A medical substance delivery device according to claim 12, wherein said picture elements make up a multi-segment display.

14. A medical substance delivery device according to claim 13, wherein said multi-segment display is an alphanumeric display.

15. A medical substance delivery device according to claim 13, wherein said multi-segment display is a cumulative area display.

16. A medical substance delivery device according to claim 15, wherein said cumulative area display comprises a plurality of picture elements making up a bar display.

17. A medical substance delivery device according to claim 15, wherein said cumulative area display comprises a plurality of picture elements of sector form making up a pie display.

18. A medical substance delivery device according to claim 7, wherein said display device comprises an electronic paper device, electrical power required to write an image on the electronic paper device being derived from said at least one transducer responding to the relative movement between the first and second members.

19. A medical substance delivery device according to claim 7, wherein each of at least one transducer includes at least one piezoelectric element.

20. A medical substance delivery device comprising:
a movable control member;
a plurality of transducers responsive to movement of said control member along a path to convert mechanical energy into electrical energy to output an electrical signal;
a drive circuit for receiving said electrical signal and for outputting an output drive signal that varies according to the extent of movement of said control member, said drive circuit comprising a plurality of conductors spaced along said path for successively receiving an electrical signal on said movement; and
a display device for receiving said output drive signal and displaying a variable image that varies consequent on said movement,
wherein said control member moves to or past a selected position during preparation or delivery of a dose, and said movement to or past said selected position is effective to deflect said plurality of transducers to convert mechanical energy of movement into electrical energy to output an output drive signal, and
wherein said display device displays an image representing an operational state of the medical substance delivery device,
wherein in use, during delivery, said control member moves in proportion to the amount of medical substance delivered, and selected ones of said transducers are energized in turn and supply an electrical signal to corresponding ones of said electrical conductors, as said control member moves, and said display device displays a cumulative indication of the amount of the medical substance delivered.

21. A medical substance delivery device comprising:
a movable control member;
a plurality of transducers responsive to movement of said control member along a path to convert mechanical energy into electrical energy to output an electrical signal;
a drive circuit for receiving said electrical signal and for outputting an output drive signal that varies according to the extent of movement of said control member, said drive circuit comprising a plurality of conductors spaced along said path for successively receiving an electrical signal on said movement; and
a display device for receiving said output drive signal and displaying a variable image that varies consequent on said movement,
wherein said control member moves to or past a selected position during preparation or delivery of a dose, and said movement to or past said selected position is effective to deflect said plurality of transducers to convert mechanical energy of movement into electrical energy to output an output drive signal,
wherein said display device displays an image representing an operational state of the medical substance delivery device, and
each of said plurality of transducers is associated with a respective one of said conductors.

22. A medical substance delivery device according to claim 21, wherein each transducer is disposed between two adjacent conductors, and is adapted to be caused to contact a selected one of said adjacent conductors dependent on the direction of movement of said control member.

* * * * *